United States Patent
Regan et al.

(10) Patent No.: US 9,697,743 B2
(45) Date of Patent: Jul. 4, 2017

(54) MONITORING SURFING

(71) Applicant: Catapult Group International Ltd, Docklands (AU)

(72) Inventors: Michael Regan, Docklands (AU); Shaun Holthouse, Docklands (AU)

(73) Assignee: CATAPULT GROUP INTERNATIONAL LTD. (AU)

( * ) Notice: Subject to any disclaimer, the term of this patent is extended or adjusted under 35 U.S.C. 154(b) by 0 days.

(21) Appl. No.: 15/303,968

(22) PCT Filed: May 11, 2015

(86) PCT No.: PCT/AU2015/000271
§ 371 (c)(1),
(2) Date: Oct. 13, 2016

(87) PCT Pub. No.: WO2015/172178
PCT Pub. Date: Nov. 19, 2015

(65) Prior Publication Data
US 2017/0032693 A1    Feb. 2, 2017

(30) Foreign Application Priority Data

May 12, 2014   (AU) ................................ 2014901741
Dec. 16, 2014   (AU) ................................ 2014905090

(51) Int. Cl.
*G09B 19/00*      (2006.01)
*A61B 5/00*       (2006.01)
(Continued)

(52) U.S. Cl.
CPC ........ *G09B 19/0038* (2013.01); *A61B 5/1118* (2013.01); *A61B 5/1122* (2013.01);
(Continued)

(58) Field of Classification Search
CPC .......................... G09B 19/0038; A61B 5/1118
(Continued)

(56) References Cited

U.S. PATENT DOCUMENTS 8,036,826 B2 * 10/2011 MacIntosh ......... A63B 24/0021
                                                            701/25
9,418,705 B2 *  8/2016 Kaps ...................... G11B 27/17
(Continued)

OTHER PUBLICATIONS

Corresponding International Search Report for PCT/AU2015/000271 dated Jul. 27, 2015.
(Continued)

*Primary Examiner* — Lars A Olson
*Assistant Examiner* — Jovon Hayes
(74) *Attorney, Agent, or Firm* — The Belles Group, P.C.

(57) ABSTRACT

A data collection system for surfing which includes a data collection device mounted on the upper torso of the surfer or on the surf board. The device includes a clock, GPS unit, three dimensional accelerometers, three dimensional gyroscopes, and a microprocessor and data store for processing the signals from the GPS unit, three dimensional accelerometers and three dimensional gyroscopes. The microprocessor is programmed to identify and collect signal data to derive information identifying one or more parameters including number of waves passed up, power of each wave, size and frequency of the waves, time when a wave is caught, number of paddles required to catch a wave, time between catching the wave and the surfer standing up, distance travelled and speed during ride, time when rider exits the wave, acceleration during each manoeuvre during the ride, g force and speed during turns.

6 Claims, 4 Drawing Sheets

Figure 1:
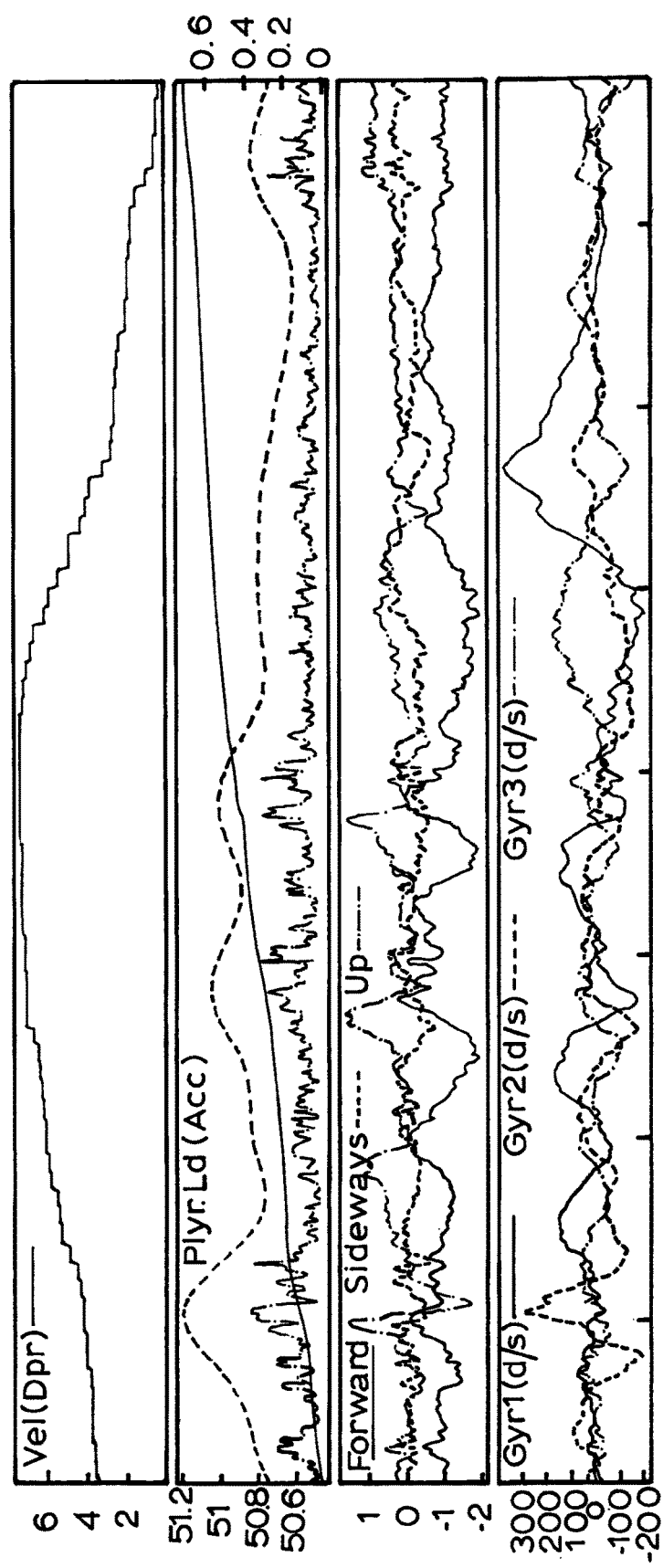

(51) Int. Cl.
*A61B 5/11* (2006.01)
*A63B 24/00* (2006.01)
*A63B 69/00* (2006.01)
*B63B 35/79* (2006.01)
*B63B 35/85* (2006.01)

(52) U.S. Cl.
CPC .......... *A61B 5/1123* (2013.01); *A61B 5/6823* (2013.01); *A61B 5/6895* (2013.01); *A63B 24/0062* (2013.01); *A63B 69/0093* (2013.01); *B63B 35/79* (2013.01); *B63B 35/85* (2013.01); *A61B 2503/10* (2013.01); *A61B 2562/0219* (2013.01); *A63B 2208/03* (2013.01); *A63B 2220/17* (2013.01); *A63B 2220/20* (2013.01); *A63B 2220/30* (2013.01); *A63B 2220/40* (2013.01); *A63B 2220/62* (2013.01); *A63B 2220/806* (2013.01); *A63B 2220/836* (2013.01)

(58) Field of Classification Search
USPC .......................................................... 441/74
See application file for complete search history.

(56) References Cited

U.S. PATENT DOCUMENTS

| 2006/0212271 | A1* | 9/2006 | Grenfell | A63B 24/0021 702/188 |
| 2012/0310587 | A1* | 12/2012 | Tu | G01D 1/16 702/141 |
| 2013/0274587 | A1* | 10/2013 | Coza | A61B 5/6804 600/409 |
| 2014/0031703 | A1* | 1/2014 | Rayner | A61B 5/02055 600/484 |
| 2017/0032693 | A1* | 2/2017 | Regan | A63B 69/0093 |

OTHER PUBLICATIONS

Dezan De Bona, A et al., "Instrumentation of a Surfboard to Evaluate Surfing Performance." 2014 11th International Conference on Remote Engineering and Virtual Instrumentation (REV), IEEE, Feb. 26-28, 2014, pp. 339-341.

Chapman, M., "Rip Curl Search GPS watch just changed your Surf Sessions forever", Apr. 18, 2014, URL: https://sur-report.co.uk/rip-curl-search-gps-watch-just-changed-your-surf-sessions-forever-676/.

* cited by examiner

MONITORING SURFING

This invention relates to a system and software for collecting and analysing data relating to wave surfing.

BACKGROUND TO THE INVENTION

Surfing is a world wide popular sport and there are many surfing competitions around the world which attract professional surfers.

The surfer, standing on a surf board rides on the forward or deep face of a moving wave, which is usually carrying the surfer towards the shore. Waves suitable for surfing are primarily found in the ocean.

In surfing competitions judging is based on the experience of the judges and is subjective. Professional and amateur surfers make judgements about waves in order to select a wave that enables riders to perform to the best of their ability. Surfers also lack objective measurements of the wave conditions and the speeds and time and action components of the ride.

Sensors have been used on motorised surf boards and surf board simulators. U.S. Pat. No. 8,290,636 relates to a motorised surf board and there is mention of displaying environmental sensor data but no detail.

Chinese patent CN01543674 discloses a surf board simulator to train a participants balance.

A similar training method is disclosed in USA 20110256518 for a remote controlled motorised surf board.

None of these prior art patents disclose the collection of surfing parameter data.

It is an object of this invention to provide a system and software for collecting data relevant to surfing and surfing competitions

BRIEF DESCRIPTION OF THE INVENTION

To this end the present invention provides a data collection system for surfing which includes
  a data collection device mounted on the upper torso of the surfer or on the surf board
  said device including a clock, GPS unit, three dimensional accelerometers, three dimensional gyroscopes, and a microprocessor and data store for processing the signals from the GPS unit, three dimensional accelerometers and three dimensional gyroscopes
  said microprocessor being programmed to identify and collect signal data to derive information identifying one or more parameters including number of waves passed up, power of each wave, size and frequency of the waves, time when a wave is caught, number of paddles required to catch a wave, time between catching the wave and the surfer standing up, distance travelled and speed during ride, time when rider exits the wave, acceleration during each manoeuvre during the ride, g force and speed during turns.

The device preferably consists of a back mounted unit with inertial sensors, accelerometers measuring 3D acceleration and gyroscopes measuring 3D rotational velocity of the upper torso. There is also a GPS providing velocity from doppler measurements. A unit of this kind is described in the applicants U.S. Pat. No. 8,036,826 the content of which is incorporated herein by reference.

The surfing parameters are derived from the signal out puts of the various sensors and the clock. The data may be presented in any suitable tabular or graphical form and may be synchronised with video of the surfer.

This will provide objective data for use in judging competitions.

The device preferably includes a wireless capability for transmitting data to a remote computer for real time analysis by a coach or spectator. The data may be synchronised with video footage to enhance broadcasting of the a surfing event.

The size power and speed of the wave selected by each competitor can be objectively measured. The number of paddles taken by each competitor to catch a wave can be measured as well as the time taken to stand up. AS well as assessing the manoeuvres of each surfer during the duration of the ride the judges will have access to objective data about the duration of the ride, the number of manoeuvres, the acceleration and G forces during the manoeuvres. Issues about wave selection and the number of waves passed up can also be objectively recorded and be used to adjudicate who is allowed to catch each wave.

The data provides objective information on obscured events such as when the surfer is in a pipe For amateur surfers the system provides objective data to help them improve their experience and skill in surfing.

Other parameters which may be measured are aerial data like flight time and height off the lip of the wave, and rotation during any manoeuvres conducted in the air, speed at entry and exit of barrel, body position on board during barrel ride, impact when falling off (wiping out), peak paddling speed, total distance covered during a surf session and number of waves caught.

All of the parameters that are measured provide an objective measure of the performance of the surfer. At present surfing competitions rely on subjective assessment and the data derived from this invention allows more objectivity to be used in comparing performances.

This system allows the distance from the start of the ride to the end of the ride as a direct distance between start and finish but it also provides the actual distance traversed and the time of the ride. A surfer when executing turns and manouvering on the wave travels further than the direct distance and this comparison along with the time taken provides an objective indication of the complexity of the ride. The algorithm also allows the number of turns and changes of direction to be identified and counted and in addition the power of the turns can be objectively measured.

In another aspect a data logger may also be incorporated into the surf board. The device may be sealed into the board to provide a waterproof protection. The device's battery may be charged inductively using an inductive charging mat or other suitable device. The data may be collected wirelessly or by transmission and can be activated remotely by wireless transmission to start the data collection cycle. In order to overcome the difficulty of retro fitting the devices into surf boards a suitable blank insert is provided to surf board makers to build into the board. The blank may then be removed and the device inserted and sealed into the board. When the device is in the board it is preferred to add a pressure sensor such as a p o tube that has an inlet in the base of the board or on the fin to measure the water pressure of the water passing over the tube. This is an indication of the velocity of the board.

With a data logger in the board other performance parameters may be measured to improve the objective measure of performance. For example the changes in the inclination of the board are indicative of the surfers manoeuvres and performance. At the beginning of the ride the board is inclined down wards and the inclination of the board may be used to identify the surfers position on the wave. When the surfer turns and is at the top of the wave the board is usually pointing upward and a measure of the vertical inclination is an indication of the quality of the manoeuvre. The height of the wave may be measured using the sensors on the board and the steepness and height of the wave and the board allow an objective measurement of the surfers manoeuvre.

The data derived from the sensors may be used to augment television broadcasting of competitions. A separate sensor may be mounted on a buoy at the competition site to provide data on all waves. A suitable location would be before the position where the waves break.

In another aspect this invention provides a method assessing performance of a surfer using the system of this invention in which the performance is assessed based on measures of the following parameters: number of waves passed up, power of each wave, size and frequency of the waves, time when a wave is caught, number of paddles required to catch a wave, time between catching the wave and the surfer standing up, distance travelled and speed during ride, time when rider exits the wave, number and type of manoeuvres during ride, acceleration during each manoeuvre during the ride, G force and speed during turns.

The data may be synchronised with video of the surfer to match the sensor signals to the visual activity of the surfer. A drone mounted camera may be used to collect the video information and the drone can be locked onto the GPS signal position from the surfer's back pack data logger so that the camera can easily follow the surfer during the ride.

DETAILED DESCRIPTION OF THE INVENTION

A preferred embodiment of the invention will now be described with reference to the drawings in which:

FIG. 1: Data set while surfer is standing.

Figure 2:
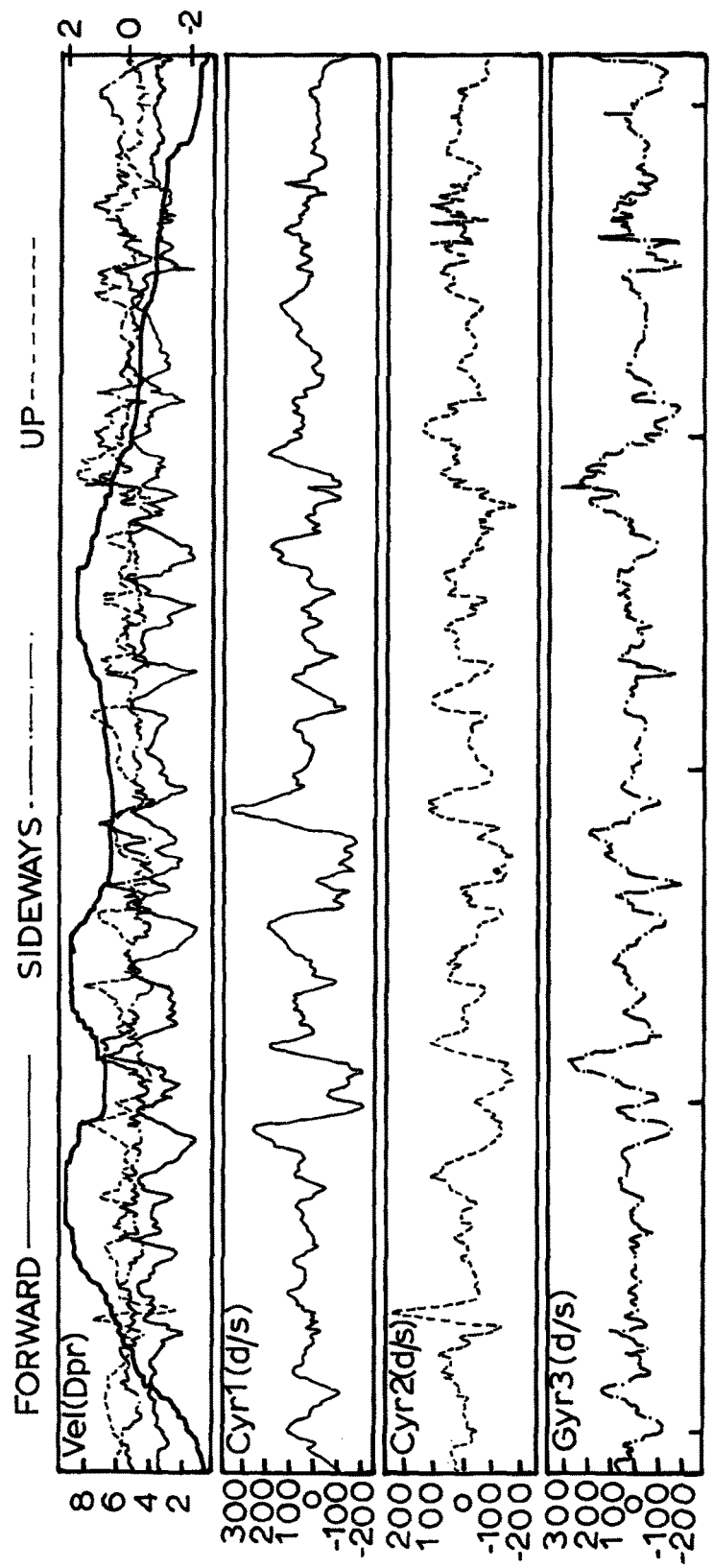

FIG. 2: Data set including pop up and wipe out

Figure 3:
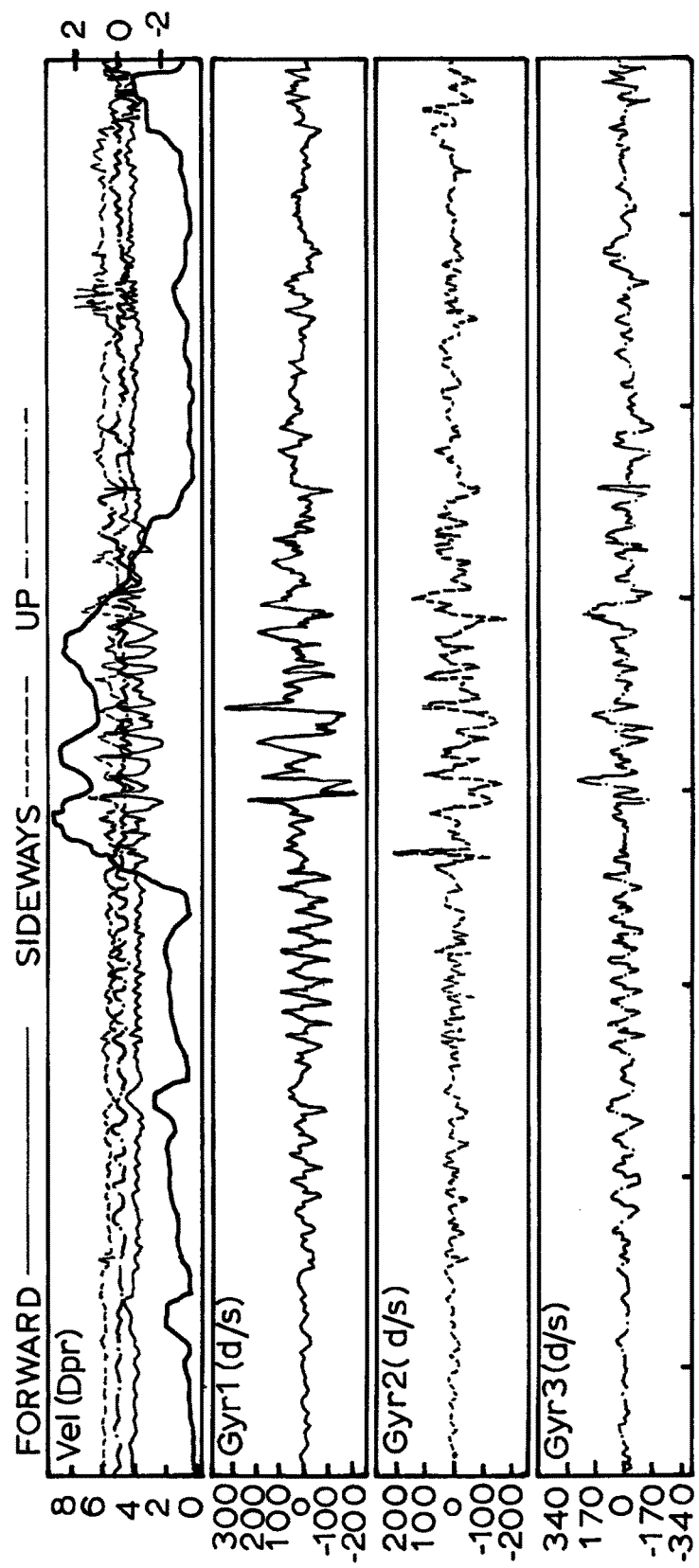
Figure 4:
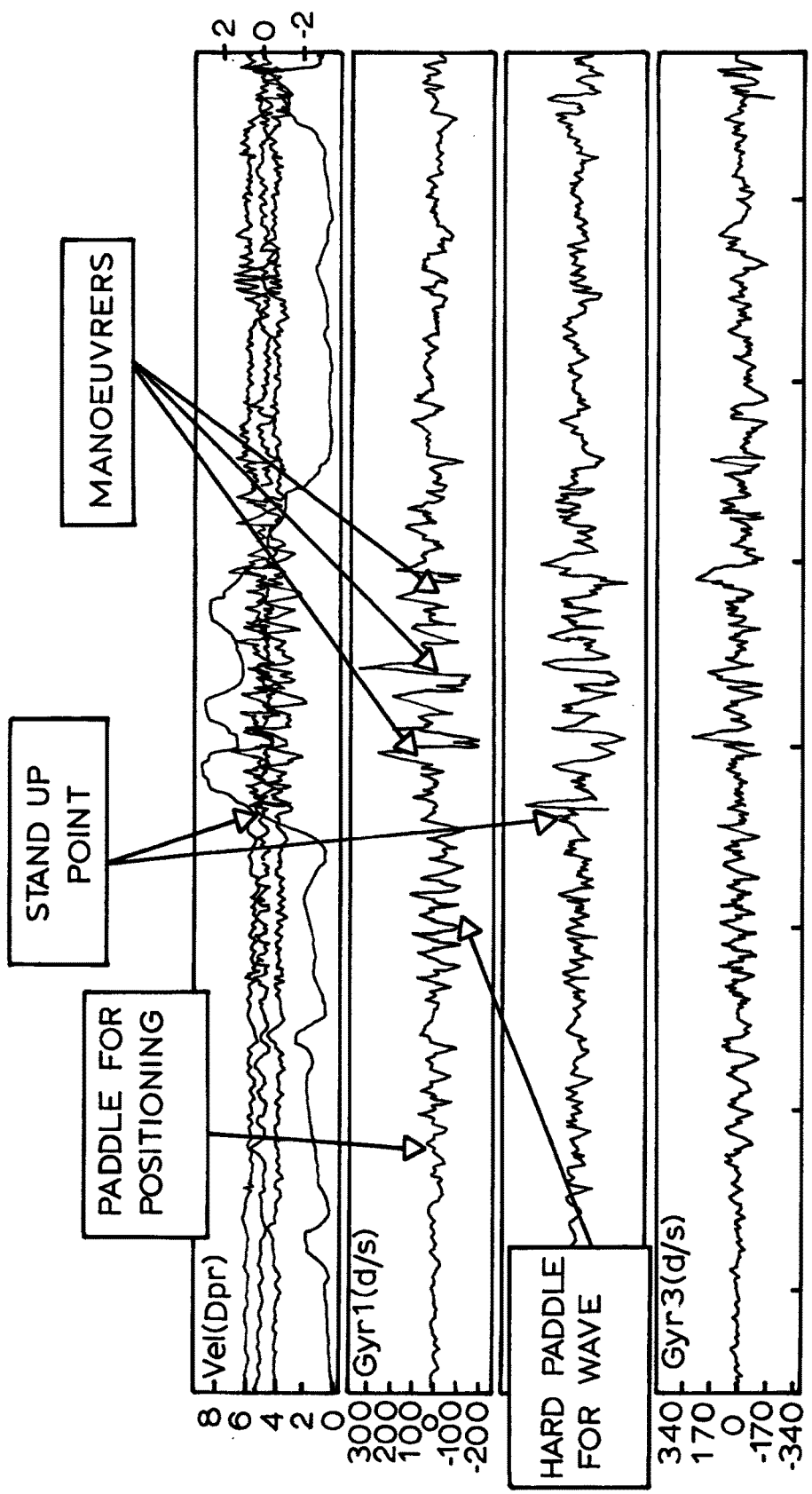

FIG. 3: Full data set including wait, paddle ride and recovery;

FIG. 4: Marked up data set showing critical features for surfing analysis.

The devices used are described in the applicants U.S. Pat. No. 8,036,826.

Position, distance travelled and average speed is derived from the GPS sensor. Wave power frequency and speed is derived from the 3 dimensional accelerometer signals. The 3 dimensional accelerometer signals are also used to identify a paddle, the points at which the surfer stands up and exits the ride. The 3 dimensional gyrometer signals and the 3 dimensional accelerometer signals are used to identify manoeuvres and measure accelerations and G forces.

EXAMPLE

For one wave, a sample data set is shown in FIGS. 1 to 4.

On this wave, the surfer has paddled 8 times to catch the wave.

The surfer pumped twice for speed—reaching a peak of 9.13 m/s before executing a snap turn off the top of the wave. This turn carried the rider through the turn at a peak rotational speed of over 200 degrees/second at a peak g force reading of 1.77 g. The second manoeuvre was a cutback, where the rider peaked at over 300 degrees/second. Finally the rider pumped for speed, hitting a peak of 8.48 m/s before hitting the shore break with a peak of 1.76 g.

This ride lasts for 17.8 seconds and covers a total distance of 116 m. Including paddling, the surfer has covered 134 m. His peak speed paddling before the wave got to him was 2.07 m/s.

Utilising the same data channels, it is possible to identify periods of flight, allowing the analysis to produce metrics such as flight time, landing force, speed at take off, rotation through the air and jump height.

GPS devices are capable of giving the altitude of the rider during a wave. This allows for a new measure of how far the athlete travels vertically during a wave. This can be applied in judging, allowing objective information on not only the size of the wave ridden, but how deep bottom turns were completed and how far up the wave face the athlete got before executing turns, both critical in determining how committed the surfer was in riding the wave.

The distance travelled on the wave can be taken in two different ways. Linear distance refers to how far the wave took the athlete from take off point to dismount. Actual distance refers to the total distance travelled including stalls, turns, drives, aerials etc. The actual distance could be used to give an indication of how much the surfer was able to do on the wave and therefore, how well they maximised its potential.

When in a barrel a surfer's signal to the satellites will be occluded and may cause a noticeable change in diagnostic information. This changes opens the possibility to automate time that the athlete spends under the lip of the wave.

The combination of speed, distance, manoeuvre power, manoeuvre rotation, aerial analysis, actual distance, linear distance, ride time, paddle time, speed into an out of manoeuvres, time under the lip and other data points described give the judges an objective layer of information that could be used in scoring performance of surfers.

From the above it can be seen that this invention provides a unique means of collating training data and collecting performance data related to surfing. Those skilled in the art will also realise that the many parameter measurements made available by this invention will provide many objective measure for comparing surfer performance.

Those skilled in the art will realise that this invention may be implemented in other embodiment than those show without departing from the core teachings of this invention.

The invention claimed is:

1. A data collection system for surfing which includes
a data collection device adapted to mounted on the upper torso of the surfer or on the surf board
said device including a clock, GPS unit, three dimensional accelerometers, three dimensional gyroscopes, and a microprocessor and data store for processing the signals from the GPS unit, three dimensional accelerometers and three dimensional gyroscopes
said microprocessor being programmed to identify and collect signal data to derive information identifying one or more parameters including number of waves passed up, power of each wave, size and frequency of the waves, time when a wave is caught, number of paddles required to catch a wave, time between catching the wave and the surfer standing up, distance travelled and speed during ride, time when rider exits the wave, acceleration during each manoeuvre during the ride, G force and speed during turns.

2. A data collection device as claimed in claim 1 wherein the microprocessor also provides outputs that display the duration of the ride, the number of manoeuvres, the acceleration and G forces during the manoeuvres.

3. A data collection device as claimed in claim 1 which includes the ability to transmit data to a remote computer.

4. A surf board which incorporates the data collection device defined in claim 1.

5. A method assessing performance of a surfer using a system a system as claimed in claim 1 in which the performance is assessed based on measures of the following parameters: number of waves passed up, power of each wave, size and frequency of the waves, time when a wave is caught, number of paddles required to catch a wave, time between catching the wave and the surfer standing up, distance travelled and speed during ride, time when rider exits the wave, number and type of manoeuvres during ride, acceleration during each manoeuvre during the ride, G force and speed during turns.

6. A method as claimed in claim 5 in which the data is synchronised with a video recording of the performance.

\* \* \* \* \*